United States Patent [19]

McGuire et al.

[11] Patent Number: 5,209,929
[45] Date of Patent: May 11, 1993

[54] **IMMUNIZATION AGAINST BABESIOSIS USING PURIFIED MEROZOITE SURFACE ANTIGENS OF *BASESIA BIGEMINA***

[75] Inventors: Travis McGuire, Pullman, Wash.; Terry McElwain, Gainsville, Fla.; Lance Perryman; William Davis, both of Pullman, Wash.

[73] Assignee: Washington State University Research Foundation, Pullman, Wash.

[21] Appl. No.: 663,255

[22] Filed: Mar. 1, 1991

Related U.S. Application Data

[63] Continuation of Ser. No. 31,328, Mar. 19, 1987.

[51] Int. Cl.$^5$ ............................................. A61K 39/018
[52] U.S. Cl. ............................................. 424/88; 514/2; 514/8; 530/350; 530/395; 530/806; 530/820
[58] Field of Search ................... 530/350, 395; 514/2, 514/8, 12; 424/88

[56] References Cited

U.S. PATENT DOCUMENTS 4,661,348  4/1987  Wright ................................. 424/88

OTHER PUBLICATIONS

I. G. Wright, et al. Jul. 1983, Infect. Immun. 41:244–50. "*B. bovis:* Isolation of a Protective Antigen by Using MAbs".

Braude, A. I. et al., (eds). 1986 Infectious Diseases and Medical Microbiology. pp. 620–621, 1265–1269.

T. F. McElwain, et al. Apr., 1987, J. Immunol. 138(7): 2298–2304. "Antibodies Define Multiple Proteins with Epitopes Exposed on the Surface of Live *B. babesis* Merozoites".

I. G. Wright et al. Feb. 1987. Infect. Immun. 55(2): 364–368, "Protection of *Babesis bigemins*-Immune Animals Against Subsequent Challenge with Virulent *Babesis bovis*".

*Primary Examiner*—Christine M. Nucker
*Assistant Examiner*—T. Cunningham
*Attorney, Agent, or Firm*—Saliwanchik & Saliwanchik

[57] ABSTRACT

Antigenic surface proteins from the intraerythrocytic merozoite stage of *Babesia bigemina* have been isolated using cell fusions and monoclonal antibodies produced thereby. Immunization of mammals, such as bovines, with purified isolates induces an immunological response that is effective to reduce pathological effects of babesiosis induced by *Babesia bigemina*. Diagnostic kits using monoclonal antibodies and antigenic surface proteins of *Babesia bigemina* are also disclosed.

11 Claims, No Drawings

IMMUNIZATION AGAINST BABESIOSIS USING PURIFIED MEROZOITE SURFACE ANTIGENS OF *BASESIA BIGEMINA*

CROSS-REFERENCE TO A RELATED APPLICATION

This application is a continuation of application Ser. No. 07/031,328, now abandoned.

TECHNICAL FIELD

This invention relates to the immunization of cattle and other animals subject to infection by the protozoan species Babesia bigemina.

BACKGROUND OF THE INVENTION

Babesiosis caused by *Babesia bigemina* is a disease primarily affecting cattle, although limited other mammals may also be subject to infection by this species of Babesia. The disease is enzootic to tropical and subtropical climates where it poses severe constraints on livestock production. The risk of the disease and losses caused by it restrict movement of cattle to and from such enzootic areas thus resulting in a lost opportunity to upgrade local herds by importation of genetically superior breeds which are susceptible to the disease. Significant losses of cattle, meat, and milk production occur from *Babesia bigemina* induced babesiosis.

Despite many years of research relating to babesiosis, effective practical vaccines or other immunoprophylaxes against *Babesia bigemina* induced babesiosis are not available to the herdsman. The most common vaccination practice in use today is premunition, which is the inoculation of susceptible animals with blood infected with parasites which have been rendered less virulent. Although premunition provides good immunity against both homologous and heterologous strain challenge, it has a number of drawbacks, including: (a) induction of a carrier state which perpetuates the protozoan life cycle in the environment; (b) variation in the vaccine virulence which results in death, abortion, or clinical disease in some vaccinates; (c) contamination of the inoculant with other blood-borne infectious agents such as bovine leukosis virus, bluetongue virus, anaplasma, and theileria; (d) cumbersome and expensive production, storage and transport procedures which render vaccination impractical in many parts of the world; and (e) contamination of the vaccinates with host erythrocytes. Various experimental vaccines using inactivated Babesia parasites only provide partial protection against homologous strain challenge and poor protection against heterologous strain challenge.

The infective form of *Babesia bigemina* is the sporozoite which is found in the salivary gland of infected *Boophilus microplus* and possibly other species of Boophilus ticks. After being introduced into the tissues of the bovine host by the bite of a tick, the sporozoites enter red blood cells (erythrocytes) of the host animal. The sporozoites multiply and develop into merozoites within the erythrocytes. Infection initiates a cycle of host erythrocyte invasion and lysis which results in the clinical disease babesiosis which can often result in death of the host. Recovery from acute babesiosis is associated with immunological response including development of long lasting protective immunity against subsequent challenge.

There remains a need to overcome the known disadvantages of prior art vaccines by developing vaccines and methods for preventing or minimizing the pathological effects of *Babesia bigemina* induced babesiosis.

DETAILED DESCRIPTION OF THE PREFERRED EMBODIMENTS

Inoculants and vaccines according to this invention include substantially pure antigenic surface proteins derived from or patterned after the merozoite stage of *Babesia bigemina*. The surface proteins useful in this invention must be capable of stimulating at least some significant immune response in the cattle or other susceptible animals being treated. The inventive immunogenic surface proteins thus have both antigenic and immunogenic effects when inoculated into the animal being treated.

The substantially pure proteins useful in this invention are advantageously identified by purifying *Babesia bigemina* merozoites from infected blood of an animal of the same species as those to be treated. This is preferably done by gradient separation of the merozoites from host erythrocytes and other blood cells and structures. This is advantageously accomplished by washing infected blood with buffer solutions, subjecting to centrifugation, and by selectively removing predominantly merozoite fractions from the gradient solutions, as described more fully hereinafter. The isolated predominantly viable merozoites are then used to generate monoclonal antibodies used to discriminate the inventive immunogenic merozoite proteins from non-immunogenic proteins which also exist in the merozoite cells.

The monoclonal antibodies are prepared by first vaccinating mice with the viable *Babesia bigemina* merozoites. Lymphocytes from the spleen of the infected mice are then obtained and fused with myeloma cells using polyethylene glycol or other appropriate cell fusing agent, to produce fused cell hybridomas. The hybridomas and their clones produce monoclonal antibodies to various antigens contained in the *Babesia bigemina* used to infect the mice.

Monoclonal antibodies from the hybridomas or their clones are then initially screened to determine which antibodies bind to surface reactive epitopes of the merozoites, such as by using indirect immunofluorescent assay of smears of *Babesia bigemina* infected blood with both fixed and viable merozoites. The monoclonal antibodies which bind to the surface the live merozoites are then further screened for reactivity using radioisotope-labeled surface proteins from the merozoites. Some of these labeled surface proteins are selectively immunoprecipitated by some of the surface-reactive monoclonal antibodies identified in the immunofluorescent assays.

The immunoprecipitated antigenic surface proteins are further analyzed to determine their molecular weight using gel electrophoresis. The molecular weights of the surface proteins immunoprecipitated by the monoclonal antibodies are then further compared and analyzed to determine the number and molecular weights of those which have surface reactive epitopes. The antigenic merozoite surface proteins are preferably further analyzed to determine which are reactive to antibodies raised in immune animals which have been infected and recovered from babesiosis caused by *B. bigemina*. This further discrimination is advantageously accomplished using immunoprecipitation of radioisotope-labeled merozoite proteins by immune sera collected from such animals. The resulting identified antigenic surface proteins can then be isolated into a purified form.

Hybridoma cell lines are used to produce the monoclonal antibodies which selectively bind to the desired proteins. The selected monoclonal antibodies can then be used to remove the desired antigenic proteins from infected blood using an immunoaffinity chromatography column or similar immunoaffinity or immunoprecipitation techniques.

Purified monoclonal antibodies most desirable for use in immunoaffinity chromatography are advantageously produced by collection of ascitic fluid from mice vaccinated with the corresponding hybridomas or clones which produce the desired monoclonal antibodies. The collected ascitic fluid is then purified, such as by precipitation and chromatography as described below. Each purified monoclonal antibody is then advantageously coupled to an insoluble matrix such as Sepharose to prepare an immunoaffinity matrix. Partially purified disrupted *Babesia bigemina* merozoites are then passed through the immunoaffinity matrices and the desired merozoite proteins are selectively adsorbed onto the individual monoclonal antibodies held by each matrix. The non-adsorbed materials are washed through the affinity chromatography column and the desired proteins recovered from the affinity chromatography column matrix, such as explained more fully below.

In research related to cattle, five monoclonal antibodies resulted in identification of at least five major immunoprecipated merozoite surface proteins having apparent molecular weights of 36, 45, 55, 58 and 72 kilodaltons (kd). Some of the monoclonal antibodies also immunoprecipitated secondary merozoite proteins. Such immunogenic proteins are herein identified as Bp 36, Bp 45, Bp 55, Bp 58 and Bp 72, respectively. Each of the above surface proteins is identified by its highest molecular weight component consistently present in both immunoprecipitates and affinity chromatograph eluates, preceded by the letters "Bp". The additional proteins bound by the monoclonal antibodies were also present in the vaccines tested and may also be immunogenic. Monoclonal antibodies identified herein as 14.52, 14.1, 14.20, 14.16, and 14.29 bound to such antigenic proteins, respectively. Four hybridoma cell lines survived cloning. Such cell lines produce monoclonal antibodies 14.1, 14.16, 14.20 and 14.52, and have been deposited with the American Type Culture Collection and are designated by deposit numbers HB 9377, HB 9379, HB 9376, and HB 9378, respectively.

The degree of purity of proteins useful in accordance with the present invention is much higher than the purity of the surface antigen in its natural state. As an example, in its natural state Bp 55 is believed to be present in an amount of about 0.1 to 1% of the total protein present in the merozoites. In its natural state, many other impurities such as about 100-200 other proteins, carbohydrates, glycoproteins, and nucleic acids can be present. However, the Bp 55 protein can be purified to a purity of at least 90 weight percent, preferably at least 95 weight percent and most preferably at least 98 weight percent. The purified Bp 55 includes a primary protein having an approximate molecular weight of about 55,000 daltons and a secondary protein having an approximate molecular weight of 43,000 daltons. The Bp55 is essentially free of contaminating proteins, glycoproteins, carbohydrates, nucleic acids and most other contaminating antigens. Similar relationships are believed to exist with respect to other immunogenic proteins or protein combinations according to this invention.

The discovered immunogenic surface proteins are also polypeptides. It is believed that an active fragment or combination of fragments of these polypeptides may be effective in inducing immunity to *Babesia bigemina* in cattle and possibly other affected animals. The size of the active fragment may be as small as six to twenty or possibly six to ten amino acids.

The purified immunogenic surface antigens or an active fragment thereof may be produced by immunoaffinity chromatography polypeptide synthesis or genetic engineering (DNA cloning with protein fragment expression).

The purified immunogenic proteins of this invention should be present in a single dose of vaccine in an amount of approximately 1-400 micrograms, preferably 5-200 micrograms, and most preferably 20-100 micrograms. A single injectable dose will usually have a volume of about 1 ml. Therefore the concentration of purified surface antigen in an injectable vaccine composition will usually be in the range of from about 1 to about 400 micrograms/ml, preferably about 5 to about 200 micrograms/ml and most preferably 20-100 micrograms/ml. Immunization using alternative inoculation techniques may require substantial adjustment in the amount of active immunogen used. Immunization of non-bovines may also require such adjustment.

Vaccines according to the invention preferably include an immunogenic adjuvant such as Freund's complete adjuvant or others which are effective. The immunogenic merozoite derived surface proteins will usually be dissolved, mixed or suspended in such an immunogenic adjuvant. The vaccine may also advantageously contain any other pharmaceutically acceptable carrier or diluent. The pharmaceutically acceptable carrier or diluent is preferably a compound, composition or solvent which is administered as a non-toxic sterile liquid.

Methods according to the invention include inoculating animals with a vaccine or other inoculant comprising a substantially pure immunogenic surface protein, an active fragment thereof, an immunologically similar protein produced by polypeptide synthesis or genetic engineering, or a combination of such antigens. Preferably, the animals being immunized are successively vaccinated by injection with a single dose as defined above at one to six week intervals, preferably two to four week intervals, about one to five times, preferably three to five times. It would be most preferable to use one or two vaccinations in commercial applications. The substantially pure protein should be present in the vaccine in an amount effective to induce at least a partial immune response to *Babesia bigemina*. When the animals are subsequently challenged with virulent *Babesia bigemina*, the degree of acute infection is substantially reduced or even prevented. Injection will usually be performed intramuscularly (i.m.) or subcutaneously (s.c.).

The isolated immunogenic proteins, an active fragment thereof, or an immunologically analogous protein or peptide produced by polypeptide synthesis or genetic engineering can also be used as the basis of diagnostic tests, such as radioisotope, fluorescent or enzyme linked immunosorbent assays for serologic diagnosis of babesiosis caused by *B. bigemina*. When blood samples from suspected animals are tested using such antigens, results distinguishing infected and non-infected animals are obtainable due to detectable levels of antibodies raised in the animal against the *B. bigemina* infection. Monoclonal antibodies used to selectively bind the immunogenic proteins can also be used in diagnostic kits.

Monoclonal antibodies according to this invention may be useful in treating animals acutely infected by *B. bigemina*. Such antibodies may be used such as by injection in the form of vaccines, using the concentrations, adjuvants and methods described herein with respect to immunizations using the immunogenic merozoite proteins.

Immunogenic surface proteins from the intraerythrocytic merozoite stage of *Babesia bigemina* have been isolated utilizing cell fusion procedures which will be discussed more fully below in the context of development of vaccines and innoculants for immunization of cattle against babesiosis from *Babesia bigemina*. Immunization of bovines with such isolates induces an immunological response which produces at least partial immunity which is useful in reducing the pathological effects of such disease in cattle.

EXAMPLE

Blood isolates from bovines infected by *Babesia bigemina* from a Mexico strain of the parasite were obtained. Each isolate was stored in liquid nitrogen as a blood stabilate containing packed erythrocytes (1:1) with a cryopreservant of 10% (w/v) polyvinylpyrollidone and 2% (w/v) glucose in Puck's Saline G, obtainable from Gibco Laboratories of Chagrin Falls, Ohio.

A. Purification of *Babesia bigemina* Merozoites.

1. Gradient Separation—The merozoites were first purified using centrifugation gradient separation in silica gel colloidal suspensions. A 20 ml stabilate of packed infected erythrocytes was thawed at 37° C. for 15 minutes, diluted to 100 ml in buffer containing 0.01M sodium phosphate, 0.15M NaCl, pH 7.2 (hereinafter PBS), and washed three times by centrifugation at 1100 G. The resulting cell pellet was suspended in 10 ml PBS and forced through a Pyrex glass wool column to remove agglutinated cells and debris. One ml aliquots of the eluate were layered on 10 ml continuous silica gel collordal suspensions, commonly known as Percoll gradients, which were generated by centrifugation of a 40% (v/v) isosmotic solution of Percoll (Pharmacia Fine Chemicals, Uppsala, Sweden) in PBS at 30,000 G for 15 minutes. Infected erythrocyte ghosts were collected from the top of each gradient and washed 3 times in PBS by centrifugation at 2500 G. The organism was maintained at 4° C. throughout such procedure.

The objective of gradient separation purification was to obtain a purified preparation of merozoites that would facilitate the identification of surface proteins therefrom. The desired parasites were separated from other fractions of the cryopreserved blood stabilates using such processing.

2. Electron Microscopy—Electron microscopy was advantageously used to evaluate the gradient separation purification of the merozoites. Cell pellets from Percoll gradients were fixed for 1 hour in 3% (v/v) gluteraldehyde in 0.1M sodium phosphate buffer, pH 7.4. They were washed twice in 0.1M sodium phosphate buffer, pH 7.4, and treated for 1 hour in 1% (v/v) osmium tetroxide in the same buffer. Following 2 additional washes in said phosphate buffer, the cell pellets were dehydrated through a graded series of ethanol washes (75%, 95%, 100%), equilibrated in propylene oxide, and embedded in Epon or other plastic materials as is well known in the art using standard procedures. Thin sections stained with uranyl acetate and lead citrate were examined on a Hitachi 600 transmission/scanning electron microscope.

Transmission electron microscopy of the gradient separated parasites revealed both intact and disrupted merozoites. Phase micrographs of the merozoite preparation obtained 1-5 mm below the top of a 40% continuous Percoll gradient demonstrated the relative purity of the merozoites so collected at more than 95% and the absence of contaminating uninfected erythrocytes, leukocytes and platelets.

Nearly all merozoites obtained from the Percoll gradient were surrounded by two cell membranes. Ana 13, a monoclonal antibody (IgM isotype) that reacts with an epitope on the membrane of normal bovine erythrocytes, bound to the outer membrane in indirect immunofluorescent assay (IFA) of live merozoites. Bovine immune serum against *Babesia bigemina* reacted with both membranes, but did not bind to uninfected erythrocytes. Normal bovine serum and control IgM isotype monoclonal antibody did not bind to erythrocyte or merozoite membranes in this assay.

3. Viability—The viability of the gradient separated merozoites was then tested using the following procedure. An aliquot of cells recovered from the Percoll gradients and suspended in PBS was mixed with fluorescein diacetate (hereinafter FDA) in PBS to a final concentration of 10 micrograms/ml. Following 15 minutes of incubation at room temperature, the mixture was diluted 1:100 with PBS and examined in a hemacytometer by phase and fluorescence microscopy. Viability was expressed as percentage of total cells that were fluorescent. The parasites were also subjected to various cytocidal treatments, including two freeze/thaw cycles at −20° C.; 10% buffered neutral formalin treatment for 30 minutes on ice; 3% gluteraldehyde treatment for 30 minutes on ice; 0.1% saponin treatment for 15 minutes at 37° C.; or heating at 56° C. for 3 minutes; in order to confirm the dependence of FDA retention on merozoite cell membranes remaining intact.

4. Infectivity—The infectivity of the gradient separated merozoites was confirmed by intravenous inoculation of 3 splenectomized Holstein calves with $5\times10^7$ or $1\times10^8$ FDA positive parasites. The inoculated animals suffered from acute clinical babesiosis indicated by elevated rectal temperatures, decreased packed cell volume (hereinafter PCV), and parasitemia (the percentage of 100 erythrocytes containing parasites in a Wright's stained blood smear).

B. Generation of Fused Cell Hybridomas and Monoclonal Antibodies

1. Lymphocytes from Mice—Eight week old BALB/c mice were immunized subcutaneously with $1\times10^7$ FDA positive parasites in 0.1 ml PBS emulsified in an equal volume of complete Freund's adjuvant. Two additional booster immunizations consisting of the same number of cells in incomplete Freund's adjuvant were given subcutaneously at 10 day intervals. The mice were then immunized intravenously 3 times at 21 day intervals with $1\times10^7$ FDA positive cells in 0.1 ml PBS, the last immunization occurring 72 hours prior to fusion. The spleens of such immunized mice were removed for use in cell fusion.

2. Myeloma Cells—Myeloma cells were selected from a HAT (hypoxanthine, aminoterin and thymidine)—sensitive, tissue-culture-adapted mouse myeloma cell line for use in the hybridoma cell fusions.

Cells from murine myeloma cell line X-63 Ag8.653, available from the American Type Culture Collection, were used in the fusions described below.

3. Cell Fusions—Spleen cells from the mice vaccinated as described above were crushed and passed through a screen to assure division. The spleen cells were then fused with the above-described murine myeloma cells at a ratio of 2.5 nucleated spleen cells to 1 myeloma cell. The cells were fused by suspending them in a 50% aqueous solution of polyethelene glycol, such as PEG-1500 available from Baker Chemicals. The fusion took place at 25° C. for approximately 3 minutes.

The solution containing the fused cells was then diluted in serum free tissue culture medium, such as Dulbeco's Modified Eagle Medium (DMEM). Cells were then plated into 96 well microculture plates in the presence of 800,000–1,000,000 thymocytes per well and approximately 1 microgram per well of salmonella typhimurium mitogen (STM) available from Riebe Immunochem of Hamilton, Mont. Also added to the cultures media was 2-mercaptoethanol to produce a concentration of $5 \times 10^{-5}$M.

Approximately 24 hours after fusion, the microcultures were supplemented by the addition of HAT media thereto. Thereafter the hybridoma cell cultures were cloned by limiting dilution using thymocytes and 2-mercaptoethanol.

The hybridoma cell lines are preferably stored in liquid nitrogen. They are cultured in Dulbeco's Modified Eagle Medium with 10% fetal bovine serum, 2 mM L-glutamine, 100 U/ml penicillin, 100 micrograms/ml streptomycin, and $3 \times 10^{-5}$M 2-mercaptoethanol at 37° C. and 5% $CO_2$.

Alternative methods for cell fusions and cloning can also be used as may presently or hereafter be known in the art.

4. Screening of Monoclonal Antibodies and Hybridomas (a) The cell fusions resulted in numerous hybridoma cell lines producing various monoclonal antibodies only some of which bound to the surfaces of the merozoites. Antibodies in hybridoma supernatants produced 2 distinct patterns of fluorescence on acetone fixed *Babesia bigemina* blood smears. Some reacted with only a portion of the erythrocytes present in a field. By phase microscopy of the same microscopy field, it was found that all fluorescent erythrocytes contained parasites. Others reacted only with the parasite, as determined by a pattern of fluorescence compatible with the morphology of *Babesia bigemina* and by comparison of the same field in phase microscopy. Cell lines producing antibodies that reacted only with the fixed parasite were expanded to 24 well plates and screened by IFA of live merozoites. Out of 65 antibodies reacting with fixed parasites, 43 bound to live merozoites. All 43 positive antibodies bound between 70% and 95% of the merozoites in a preparation with a viability of 70%. Reaction of the merozoite preparation with both Ana 13 (monoclonal antibody against normal bovine erythrocytes) and a monoclonal antibody against the parasite surface, produced fluorescence on both the inner parasite membrane and the outer erythrocyte membrane. Supernatants from the initial fusions and from limiting dilution clones produced therefrom were screened to produce the results indicated above by indirect immunofluorescence assay using acetone fixed and live *Babesia bigemina* organisms as described below.

(b) Indirect Immunofluorescence Assay (IFA)—Fixed *Babesia bigemina*

Indirect immunofluorescence of acetone fixed *Babesia bigemina* was performed such as described by T. C. McGuire, G. H. Palmer, W. L. Goff, M. I. Johnson, and W. C. Davis (1984), "Common and Isolate-Restricted Antigens of *Anaplasma marginale* Detected with Monoclonal Antibodies", *Infect. Immun.* 45:697, which is incorporated hereinto by reference. Blood smears from *Babesia bigemina* experimentally infected animals were fixed in acetone for 5 minutes, and incubated with hybridoma supernatants containing the monoclonal antibodies. In assays involving antibodies raised in immune cattle, bovine serum was incubated with the fixed parasites instead of the monoclonal antibodies. Both were diluted in PBS for 30 minutes at room temperature. The incubated smears were thereafter washed 3 times with PBS. Antibodies which directly bound to the merozoites were detected by binding a labeled second antibody conjugate thereto, such as fluorescein isothyocyanate conjugated to a second antibody (rabbit anti-mouse or rabbit anti-bovine immunoglobulin). Slides were examined on a Zeiss microscope equipped for epifluorescence with a mercury lamp.

(c) Indirect Immunofluorescence Assay (IFA)—Live *Babesia bigemina*

All steps were performed on ice. Gradient separated *Babesia bigemina* merozoites were suspended in PBS containing 0.5% (w/v) bovine serum albumin (hereinafter BSA). Aliquots of $1\times10^7$ FDA positive cells were centrifuged at 2500 G for 5 minutes and resuspended in monoclonal antibody supernatant containing 25 micrograms immunoglobulin or in 100 microliters serum diluted in PBS/BSA by centrifugation at 2500 G. Bound antibodies were detected by incubation for 30 minutes in fluorescein isothyocyanate labeled rabbit anti-mouse or rabbit-anti-bovine conjugate followed by washing as described above in the fixed assay. The cell pellet was examined in a wet mount by phase and fluorescence microscopy. Percentage of merozoites bound by monoclonal antibody was calculated by determining the number of fluorescent cells in 500 total cells. Uninfected bovine erthrocyte ghosts were used as control antigen in live IFA.

C. Identification of *Babesia bigemina* Surface Proteins with Exposed Epitopes

Monoclonal antibodies were selected which bound to at least 70% of the parasites in an IFA of live merozoites with viability of 70%. The resulting 43 monoclonal antibodies were further screened by radioimmunoprecipitation of $^{35}$S-methionine metabolically labeled *Babesia bigemina* using procedures as described below.

1. Metabolic Radiolabeling of Parasites—Heparinized blood collected from a splenectomized calf infected with the Mexico stabilate of *Babesia bigemina* was harvested at the time of logarithmic parasite growth. The blood was washed twice in calcium and magnesium free Hank's balanced salt solution (hereinafter HBSS) by centrifugation at 800 G for 10 minutes. The buffy coat and 50% of the packed erythrocyte pellet was removed at each wash. The resulting cell pellet was resuspended to 50% (v/v) with HBSS, and 5 ml aliquots were layered on 40 ml 60%/80% Percoll step gradients prepared by centrifugation at 1000 G for 30 minutes and made isosmotic with HBSS. After centrifugation at 500 G for 30 minutes, the erythrocyte pellet at the bottom of the tube was collected, washed 2 times with HBSS, and resuspended to $2 \times 10^9$ erythrocytes/ml in either: Medium-199 without D,L-Methionine and sodium bicarbonate (Gibco Laboratories, Chagrin Falls, Ohio); Eagle Minimal Essential Medium modified with Earle's salts without L-glutamine and D,L-methionine (Flow Laboratories, McLean, Va.); or RPMI-1640 Select-Amine Medium without D,L-methionine (Gibco Laboratories, Chagrin Falls, Ohio). Each medium, pH 7.0, also contained 2 mM L-glutamine, 10% (v/v) fetal bovine serum, 100 units/ml penicillin, and 200 micrograms/ml streptomycin. Pooled, uninfected blood from 5 normal calves was processed exactly as infected blood. Total erythrocyte counts, total white blood cell counts, percentage leukocyte contamination, presence and number of reticulocytes (as determined in smears of 0.5% new methylene blue stained cells), and parasitemia were determined on aliquots of the parasitized erythrocytes in media.

A merozoite cell suspension was prepared therefrom using $^{35}$S-methionine at a concentration of 100 microCi/$3 \times 10^9$ erythrocytes, and was cultured in a candle jar using a procedure such as described by P. Timms, (1980), "Short Term Cultivation of Babesia Species, *Res. Vet. Sci.* 29:102, which is incorporated hereinto by reference. Cultures were incubated for 3-9 hours, washed 5 times with HBSS, lysed in buffer containing 50 mM Tris (tromethamine), 5 mM ethylenediamine tetraacetic acid (EDTA), 5 mM iodoacetamide, 1 mM phenylmethylsulfonylfluoride, 0.1 mM N-alpha-rhotosyl-L-lysyl chloromethyl ketone, and 1% (v/v) Nonidet P-40 (lysis buffer), and frozen at $-70°$ C. until use. Trichloroacetic acid precipitable radioactive counts of the resulting radiolabeled parasites were determined by filter paper techniques.

2. Iodination of Erythrocyte Ghosts: Washed normal bovine erythrocytes pooled from 5 calves were lysed and labeled with Na$^{125}$I by lactoperoxidase catalyzed iodination such as described by G. H. Palmer and T. C. McGuire (1984), "Immune Serum Against *Anaplasma Marginale* Initial Bodies Neutralizes Infectivity for Cattle", *J. Immunol.* 133:1010, which is hereby incorporated by reference. The procedure was slightly modified by separation of labeled cells from free iodine prior to dialysis through a 4 ml Dowex 1-X8-200 column (Bio-Rad Laboratories, Richmond, Calif.) equilibrated in PBS. Dialyzed samples were mixed with twice their volume of lysis buffer and frozen at $-70°$ C. until use.

3. Radioimmunoprecipitation Immunoprecipitation of radiolabeled antigen was performed as is known in the art, such as described by G. H. Palmer and T. C. McGuire (1984), "Immune Serum Against *Anaplasma Marginale* Initial Bodies Neutralizes Infectivity for Cattle", *J. Immunol.* 133:1010. Radiolabeled antigen was centrifuged at 135,000 G for 9 hours, passed through a 0.45 micron filter and sonicated 4 times at 75 watts for 15 seconds each. One million to 2 million TCA precipitable counts were incubated with 5 micrograms of monoclonal antibody or 5 microliters bovine immune serum for 30 minutes. Immune complexes were precipitated by the addition of second antibody (rabbit anti-murine immunoglobulin or anti-bovine IgG$_1$ and IgG$_2$) and 10% (v/v) protein A bearing *Staphylococcus aureus* (Calbiochem-Behring Corp., La Jolla, Calif.). Washing and elution of bound antigen was performed as also described by G. H. Palmer and T. C. McGuire (1984), "Immune Serum Against *Anaplasma Marginale* Initial Bodies Neutralizes Infectivity for Cattle", *J. Immunol.* 133:1010.

For electrophoresis of unreduced proteins, precipitated antigen was boiled in sample buffer without beta-mercaptoethanol. Prior to application of the unreduced sample to a sodium dodecyl sulfate polyacrylamide gel electrophoresis (hereinafter SDS-PAGE) gel, 1.5 mM iodoacetate was added at a ratio of 1 part iodoacetate to 10 parts antigen in sample buffer such as described by A. Johnstone and R. Thorpe (1982), "Polyacrylamide Gel Techniques", *Immunochemistry in Practice*, Blackwell Scientific Publications, Boston, p. 141, which is hereby incorporated by reference. Samples were either frozen at $-70°$ C. until used or loaded directly onto SDS-PAGE gels.

4. Sodium Dodecyl Sulfate Polyacrylamide Gel Electrophoresis (SDS-PAGE)-Metabolically radiolabeled parasitic antigen or immunoprecipitates were mixed with 3 times volume of SDS-PAGE sample buffer to a final concentration of 25 mM Tris, pH 6.8, 2% (w/v) sodium dodecyl sulfate, 15% (v/v) glycerol, 2.5% beta-mercaptoethanol, and a few crystals of bromophenol blue. They were boiled for 3 minutes and electrophoresed in a 7.5% to 17.5% SDS-PAGE gradient slab gel with a 5% stacking gel such as described by B. Takacs (1979), "Electrophoresis of Proteins in Polyacrylamide Gels", *Immunological Methods*, edited by T. Lefkovitz and B. Persin, Academic Press, New York, p. 81, which is incorporated by reference hereinto. The SDS-PAGE gels were processed for autoradiography. $^{14}$C-labeled proteins used for molecular weight comparisons (Amersham, Arlington Heights, Ill.) consisted of myosin, 200,000 m.w.; phosphorylase b, 92,500; bovine serum albumin, 69,000; ovalbumin, 46,000; carbonic anhydrase, 30,000; and lysozyme, 14,300. For visualization of unlabeled proteins in SDS-PAGE, gels were stained with either 0.075% Coomassie blue or silver nitrate as described by B. Takacs (1979), "Electrophoresis of Proteins in Polyacrylamide Gels", *Immunological Methods*, edited by T. Lefkovitz and B. Persin, Academic Press, New York, p. 81; and J. H. Morrissey (1981), "Silver Stain in Proteins in Polyacrylamide Gels: a Modified Procedure with Enhanced Uniform Sensitivity", *Anal. Biochem.*, 117:307, respectively. Molecular weight standards used in Coomassie blue and silver stained gels (Pharmacia Inc., Piscataway, N.J.) consisted of phosphorylase b, 94,000 m.w.; bovine serum albumin, 67,000; ovalbumin, 43,000; carbonic anhydrase, 30,000; soybean trypsin inhibitor, 20,100 and alpha-lactalbumin, 14,400. Alternative electrophoretic or other analyses may also be used for establishing molecular weights.

Nineteen of the 43 IFA surface reactive monoclonal antibodies immunoprecipitated a protein labeled with $^{35}$S-methionine. Five hybridoma cell lines identified as—14.1, 14.16, 14.20, 14.29, and 14.52—were selected for further study and were cloned by limiting dilution. These cell lines produced monoclonal antibodies that precipitated major surface proteins with relative molecular weights in SDS-PAGE of 72 kd, 58 kd, 55 kd, 45 kd, and a group of three proteins at 36 kd, 20 kd, and 16 kd. None of the monoclonal antibodies immunoprecipitated a Na$^{125}$I labeled normal bovine erythrocyte protein. Table I summarizes the specificities of these 5 monoclonal antibodies in immunoprecipitation.

TABLE I

Surface reactive monoclonal antibodies against *Babesia bigemina*

| Monoclonal Antibody | Isotype | Protein Group | Protein Specificity[a] | |
|---|---|---|---|---|
| | | | Major[b] | Additional[c] |
| 14.1 | IgG$_{2a}$ | Bp45 | 45 kd | 49, 36 kd |
| 14.20 | IgG$_1$ | Bp55 | 55 kd | 43 kd |
| 14.29 | IgG$_1$ | Bp72 | 72 kd | — |
| 14.16 | IgG$_1$ | Bp58 | 58 kd | 36, 35, 33 kd |
| 14.52 | IgG$_1$ | Bp36 | 36, 20, 16 kd | — |

[a] as determined by immunoprecipitation of $^{35}$S-methionine labeled *Babesia bigemina*
[b] immunoprecipitated from all antigen preparations
[c] immunoprecipitated from some antigen preparations Monoclonal antibody 14.52 consistently immunoprecipitated multiple proteins. Three surface reactive monoclonal antibodies—14.1, 14.16 and 14.20—each immunoprecipitated additional $^{35}$S-methionine labeled proteins when antigens from different labelings were used under the same labeling conditions. The molecular weights of these precipitated proteins are as follows: monoclonal antibody 14.1–49 kd and 36 kd; monoclonal antibody 14.16–36 kd, 35 kd, and 33 kd; and monoclonal antibody 14.20–43 kd. In addition, the relative mobility of the major protein precipitated from the merozoite antigens by monoclonal antibody 14.20 varied from 58 kd to 55 kd. Under non-reducing conditions, all immunoprecipitated proteins migrated identically to those electrophoresed under reducing conditions.

Two of the antibodies that immunoprecipitated more than one radiolabeled antigen, 14.1 and 14.16, bound to gradient separated merozoite proteins transferred to nitrocellulose. Monoclonal antibody 14.1 recognized only one band with a relative mobility of 45 kd, while monoclonal antibody 14.16 recognized immunoprecipitated proteins 58, 36, 35, and 33 kd, as well as proteins at 47 and 43 kd that were not precipitated. The two additional monoclonal antibodies that immunoprecipitated multiple proteins, 14.20 and 14.52, failed to react with merozoite proteins on nitrocellulose.

D. Identification of Proteins Recognized by Bovine Immune Sera

Immune bovine serum obtained from a calf experimentally infected with the Mexico isolate of *Babesia bigemina* was used to immunoprecipitate $^{35}$S-methionine labeled proteins from the Mexico isolate. Serum from day 25 post-inoculation (immediately following complete recovery of the calf from acute clinical babesiosis) immunoprecipitated approximately 40 radiolabeled proteins. These included proteins having approximate molecular weights of 72 kd, 58 kd, 55 kd, 45 kd, and 36 kd. Using the same radiolabeled antigen (Mexico isolate), immune bovine serum obtained from a calf experimentally infected with the Kenya isolate of *Babesia bigemina* immunoprecipitated 5 proteins that electrophoresed with relative mobilities identical to those recognized by immune serum against the Mexico isolate. When bovine immune serum and monoclonal antibody precipitates were electrophoresed in adjacent SDS-PAGE lanes, the proteins containing surface exposed epitopes recognized by monoclonal antibodies co-migrated with major proteins recognized by bovine immune serum.

Five major $^{35}$S-methionine labeled proteins migrating at molecular weights of 72, 58, 55, 45, and 36 kd in SDS-PAGE are immunoprecipitated by monoclonal antibodies surface reactive to the merozoites of *B. bigemina*. The inability of these same monoclonal antibodies to immunoprecipitate iodinated normal erythrocyte proteins, the absence of radiolabel incorporation in normal erythrocyte cultures, and the relative lack of cells (reticulocytes, leukocytes, and platelets), other than parasites, capable of methionine incorporation in *Babesia bigemina* cultures indicates that the surface proteins are of babesial origin.

In the absence of beta-mercaptoethanol and the presence of iodoacetate, *Babesia bigemina* surface proteins migrate exactly as they do in the presence of beta-mercaptoethanol, demonstrating that they are not disulfide-bonded subunits of multimeric proteins. By western blotting, monoclonal antibody 14.1 binds only to a 45 kd protein, indicating that the additional proteins co-precipitated by this antibody are part of a membrane complex not disrupted by NP-40 detergent. However, as demonstrated in western blots, all proteins immunoprecipitated by monoclonal antibody 14.16 contain the epitope to which this antibody binds and thus are specifically precipitated by it.

The antigenic surface proteins Bp 36, Bp 45, Bp 55, Bp 55, Bp 58, and Bp 72 are protease sensitive. As such they can easily be mimicked by synthetic peptides or polypeptides expressed in a foreign bacterium, yeast or virus containing the gene coding for the epitopes. Availability of the corresponding monoclonal antibodies as shown in Table I above makes synthetic peptide and gene cloning procedures practical alternatives for production of vaccines according to this invention.

E. Preparation of Vaccine and Immunization of Cattle with Purified Antigenic Surface Proteins of the Merozoite Stage of *Babesia bigemina*

1. Vaccine Preparation—Mexico isolate of *Babesia bigemina* cryopreserved as described above was utilized in preparation of a vaccine. Gradient polyacrylamide gel techniques, SDS-PAGE sample buffer, and autoradiography techniques were also utilized as described above.

Monoclonal antibodies 14.1, 14.16, 14.20, and 14.52 that recognize *Babesia bigemina* merozoite surface proteins were prepared as described above. Monoclonal antibody 14.72 was lost in dilution cloning. Ascitic fluid was generated by intraperitoneal inoculation of pristane primed BALB/c mice with a 5×10$^6$ twice cloned hybridoma cells for each of the four remaining monoclonal antibodies. Purification of monoclonal antibodies from such ascitic fluid was performed by diethylaminoethyl cellulose chromatography (DE-52, Whatman Ltd, Maidstone Kent, England) of 50% ammonium sulfate precipitated immunoglobulin (from ascitic fluid) in 0.032M Tris, pH 7.4. Columns were eluted by 0.032M Tris, pH 7.4, followed by a gradient of 0 to 0.2M NaCl in the same buffer. Protein content of 5 ml fractions from the columns was monitored by OD$_{280}$. Purity of the isolated monoclonal antibodies was further established in Coomassie blue stained gradient polyacrylamide gels (as above) loaded in each lane with 50 micrograms of protein from column fractions. Other suitable procedures for purification and purity assurance can alternatively be used.

These purified monoclonal antibodies in 0.1M NaHCO$_3$, 0.5M NaCl, pH 8.3 were rotated at room temperature for 2 hours with cyanogen bromide (CNBr)-activated Sepharose 4B beads (Pharmacia Fine Chemicals, Uppsala, Sweden) that had been washed with 0.001N HCl. Antibodies were added at a ratio of 10 mg protein to 1 ml swollen beads. Non-specific binding sites were blocked by rotating coupled beads for 2 hours at room temperature in 0.2M glycine, pH 8.0. They were then washed 3 times each with alternating buffers of 0.1M sodium acetate, 1.0M NaCl, pH 4.0; and 0.1M NaHCO$_3$, 0.5M NaCl, pH 8.3; and stored at 4° C. in buffer containing 50 mM Tris, 5 mM EDTA, 5 mM iodoacetamide, 1 mM phenylmethylsulfonylfluoride (hereinafter PMSF), and 0.1 mM N-alpha-rho-tosyl-L-lysyl chloromethyl ketone.

Immunoaffinity chromatography techniques were then performed using the purified monoclonal antibodies on the Sepharose bead matrices for each of the four monoclonal antibodies. Specifically, whole blood collected from splenectomized calves experimentally infected with the Mexico isolate of Babesia bigemina was collected at peak parasitemia, washed three times with PBS to remove leukocytes, and stored at −70° C. as a blood stabilate containing packed erythrocytes 1:1 (v/v) with a cryopreservant of 10% (w/v) polyvinylpyrollidone and 2% (w/v) glucose (crude antigen). This crude antigen was thawed at 37° C., diluted with cold PBS containing 0.1 mM PMSF, and washed three times with the same buffer at 22,000 G. The cell pellet was solubilized in buffer containing 50 mM Tris, 5 mM EDTA, 5 mM iodoacetamide, 1 mM PMSF, 0.1 mM N-alpha-rho-tosyl-L-lysyl chloromethyl ketone, and 1% (v/v) Nonidet P-40 (lysis buffer) on ice for 1 hour. Crude solubilized antigen was centrifuged for 1 hour at 135,000 G, filtered through a 0.45 micron membrane, and sonicated two times at 100 watts, 1 minute each, on ice with a Braun-sonic 1510 ultrasonicator (Braun Instruments, San Francisco, Calif.).

The solubilized antigens prepared from the infected blood was passed twice through the four monoclonal antibody-coupled Sepharose 4B columns hooked in series (750 microliters of packed wet beads each) at a flow rate of 25 ml/hour. The columns were washed sequentially with a solution containing 0.02M Tris, 0.005M EDTA, 0.1M NaCl, 0.015M NaN$_3$, pH 7.6 (hereinafter TEN) containing 1% (v/v) NP-40 and 0.1 mM PMSF; and TEN with 0.1 mM PMSF but without NP-40 detergent. They were then pre-eluted individually with 10 ml of 0.1M glycine-NaOH, 1M NaCl, 0.5% (w/v) deoxycholate, pH 10.0. Bound merozoite proteins were eluted from individual columns with 5 ml of 0.05 M diethylamine, 0.5% (w/v) deoxycholate, pH 11.5 directly into siliconized test tubes containing 0.5 ml of 1 M Tris, pH 8.5; and dialyzed against PBS to remove diethylamine and detergent. The amount of protein in the dialyzed eluates were assayed. Purity of the eluted proteins was established in silver stained polyacrylamide gels loaded with 5 micrograms protein/lane. $^{35}$S-methionine biosynthetically labeled Babesia bigemina proteins were also purified by immunoaffinity chromatography exactly as above.

2. Immunization of Cattle—Four different immunogenic agents containing surface proteins of Babesia bigemina protein groups (protein groups Bp58, Bp55, Bp45, and Bp36) were purified by monoclonal antibody immunoaffinity chromatography as described above. Twenty-five 3 month old Holstein calves were randomly assigned to 5 groups of 5 calves each. Each group was immunized intramuscularly with 1 of the 4 purified protein groups or with ovalbumin, 50 micrograms/calf, in 1 ml Freund's complete adjuvant, followed by intramuscular immunizations with 50 micrograms of the same protein in 1 ml of Freund's incomplete adjuvant at 2 week intervals until 5 total immunizations had been administered. One week following the last immunization, all calves were challenged by intravenous inoculation of freshly collected, heparinized whole blood containing $3 \times 10^9$ blood stage B. bigemina from a splenectomized calf experimentally infected with the Mexico isolate. Experimental animals were monitored by daily determination of rectal temperature, packed cell volume (PCV), parasitemia (as determined by calculating the percentage of 1000 erythrocytes containing parasites in a modified Wright's stained blood smear), and the presence or absence of hemoglobinuria. All calves immunized with a merozoite surface protein responded by production of antibodies thereto as shown by the ELISA described below.

Samples of immunized calf blood were also analyzed by immunoprecipitation of $^{35}$S-methionine labeled parasites as described hereinabove. $^{35}$S-methionine biosynthetically labeled Babesia bigemina was prepared and immunoprecipitation of radioactive antigen were performed as described above. The immune sera identified the major proteins present in the vaccines prepared as described. Additional proteins present in the Bp 58 antigen (36, 35 and 33 kd) and the Bp 36 antigen (20 and 16 kd) were also recognized by the sera from calves immunized with these antigens. A 72 kd protein not seen in immunoprecipitation or affinity purification using monoclonal antibody 14.20 was precipitated by sera from calves immunized with Bp 55. Sera from ovalbumin immunized calves did not precipitate a radiolabeled protein.

Calves immunized with Bp 36, Bp 45, Bp 55, and Bp 58 experienced reduced peak parasitemia after challenge when compared to ovalbumin inoculated calves. Calves immunized with purified merozoite proteins Bp 45, Bp 55 and Bp 36 experienced less temperature increase associated with babesiosis when compared to the ovalbumin inoculated control group. There was also some indication that immunization using Bp 36, Bp 45, Bp 55 and Bp 58 may reduce erythrocyte loss experienced by the challenged calves. Additionally, 4 of 5 ovalbumin inoculated calves experienced hemoglobinuria, whereas only 1 to 5 Bp 55 and 0 of 5 Bp 45 immunized calves had detectable hemoglobinuria after challenge. The results clearly demonstrate that immunization with the novel purified merozoite surface proteins can significantly reduce risks associated with this disease.

F. Enzyme linked immunosorbent assay (ELISA)

Sera collected from experimental animals after immunizations 3, 4, and 5 were titered by ELISA against their respective immunogens. Microtiter plates were coated with 25, 50, and 100 ng/well of purified Bp 45, Bp 58, Bp 55, and Bp 36 proteins. respectively, in 50 microliters of coating buffer (0.015 M Na$_2$CO$_3$, 0.035 M NaHCO$_3$, pH 9.6). Plates were blocked with PBS containing 1% (w/v) bovine serum albumin (PBS-BSA) for 2 hours at 37C. and rinsed 5 times with PBS containing 0.2% (v/v) Tween-20 (Sigma Chemical Co., St. Louis, Mo.) (PBS-Tween). Dilutions of serum in 50 microliters of PBS-BSA were added to each well, incubated for 1 hour, and the wells washed 5 times with PBS-Tween. Bound antibody was detected by addition of 50 microliters of peroxidase conjugated rabbit anti-bovine antibody diluted in PBS-BSA applied to each well for 1 hour, rinsing the wells as above, and adding 50 microliters of 5-aminosalicylate containing 0.005% (v/v) H$_2$O$_2$. The amount of color change was monitored by determining the OD$_{450/630}$ in an MR 600 Microplate Reader.

Diagnostic kits in accordance with this invention will typically utilize an antigenic protein which selectively binds to antibodies raised in animals exposed to *B. bigemina*. It is also possible to selectively detect antigens using monoclonal antibodies but such is not typically practical since better results will be obtainable when detecting the antibodies raised in the animals.

Diagnostic kits in accordance with the invention can be prepared as just described by coating a well or other surface with the antigen or antigens which specifically bind the antibody to be detected. Alternatively, it is possible to coat a well or other surface with monoclonal antibody or antibodies which bind prepared antigens, which in turn bind serum antibodies to be detected.

The bound serum antibodies can be detected by using an enzyme-linked antibody which binds the serum antibody, such as described above. Alternatively, it is possible to use radiolabelled secondary antibodies, fluorescent labeled secondary antibodies or other labeling techniques which now exist or are hereafter developed for the same purposes.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A method of treating a bovid to reduce the severity of babesiosis caused by *Babesia bigemina* consisting essentially of inoculating the bovid with a substantially purified *Babesia bigemina* protein immunogen selected from the group consisting of the merozoite surface proteins with the approximate molecular weights of 58,000, 55,000 and 45,000 Da.

2. The method of claim 1 wherein said *Babesia bigemina* immunogen is identifiable using monoclonal antibodies produced by at least one hybridoma cell line selected from the group consisting of the hybridoma cell lines identified by American Type Culture Collection numbers HB 9376, HB 9377, HB 9378, and HB 9379.

3. The method, according to claim 44 or claim 2, wherein said *Babesia bigemina* protein has an approximate molecular weight of 58,000 Da.

4. The method, according to claim 44 or claim 2, wherein said *Babesia bigemina* protein has an approximate molecular weight of 55,000 Da.

5. The method, according to claim 44 or claim 2, wherein said *Babesia bigemina* protein has an approximate molecular weight of 45,000 Da.

6. The method of claim 1 wherein the step of inoculating occurs in the form of a vaccine; said vaccine further comprising a pharmaceutically acceptable carrier or diluent.

7. The method of claim 6 wherein the pharmaceutically acceptable carrier or diluent includes an immunogenic adjuvant for promoting an immune response in the mammal.

8. A composition consisting essentially of at least one immunogenic substantially pure protein of *Babesia bigemina*, which when inoculated into a bovid is capable of inducing an immune response in said bovid which reduces the severity of babesiosis caused by *Babesia bigemina* wherein said immunogenic protein is selected from the group consisting of proteins having approximate molecular weights of 58,000, 55,000, and 45,000 Da.

9. The composition, according to claim 8, wherein said immunogenic protein has an approximate molecular weight of about 58,000 Da.

10. The composition, according to claim 8, wherein said immunogenic protein has an approximate molecular weight of about 55,000 Da.

11. The composition, according to claim 8, wherein said immunogenic protein has an approximate molecular weight of about 45,000 Da.

* * * * *

UNITED STATES PATENT AND TRADEMARK OFFICE
CERTIFICATE OF CORRECTION

PATENT NO. : 5,209,929
DATED : May 11, 1993
INVENTOR(S) : Travis C. McGuire et al It is certified that error appears in the above-indentified patent and that said Letters Patent is hereby corrected as shown below:

Column 1, line 3, should read --This invention was made with government support under USAID Grant Nos. DAN-4178-A-00-7056-00,DHR-5600-G-00-1035-00, and HRN-5600-G-00-2034-00;USDA Grant Nos. NRICGP-92037204-1880,88-34135-3508, and 86-CR SR-2-2842; and USDA-BARD Grant Nos. US-1855-90RC and US-1080-86. This government has certian rights in this invention.--; line 14: "Babesia Bigemina" should read --Babesia bigemina--.
Column 5, line 13, "merozoitc" should read --merozoite--.
Column 7, line 47, "microscopy field" should read --microscope field--.
Column 9, line 67, "J. Immunol," should read --J. Immunol.--.
Column 10, line 5, "electrophonesis" should read --electrophoresis--.
Column 14, line 40, "1 to 5" should read 1 of 5--; "Bp36 proteins." should read Bp36 proteins,--.
Column 16, line 6, "claim 44 or claim 2"; "claim 44 or claim 2" should read --claim 1 or claim 2 --.

Signed and Sealed this

Nineteenth Day of April, 1994

Attest:

BRUCE LEHMAN

Attesting Officer

Commissioner of Patents and Trademarks